United States Patent [19]

Ginder

[11] 4,407,662

[45] Oct. 4, 1983

[54] METHOD OF REMOVING WATER FROM ETHANOL

[75] Inventor: William F. Ginder, Houston, Tex.

[73] Assignee: Ad-Pro Industries, Inc., Houston, Tex.

[21] Appl. No.: 383,612

[22] Filed: Jun. 1, 1982

Related U.S. Application Data

[63] Continuation of Ser. No. 198,370, Oct. 20, 1980, abandoned.

[51] Int. Cl.³ .......................... B01D 3/00; B01D 53/04
[52] U.S. Cl. ............................................ 55/33; 55/35; 203/19; 203/41
[58] Field of Search ................. 203/19, 41; 55/32, 33, 55/35, 25, 26

[56] References Cited

U.S. PATENT DOCUMENTS 2,137,605 11/1938 Derr ........................................ 203/19
3,122,486 2/1964 Skarstrom ............................. 203/18

Primary Examiner—Frank Sever
Attorney, Agent, or Firm—Vaden, Eickenroht, Thompson, Bednar & Jamison

[57] ABSTRACT

A method is provided for removing sufficient water from $H_2O$ ethanol at least 160 proof to produce ethanol having a proof of 195 or more comprising the steps of heating the ethanol water mixture until it is a vapor with sufficient superheat to maintain the vapor phase and prevent substantial capillary adsorption as the mixture passes through a dessicant bed of molecular sieves, passing the superheated ethanol water mixture through the bed to remove sufficient water to increase the proof of the ethanol of at least 195, passing a portion of the dehydratedethanol through a second dessicant bed of molecular sieves at less than atmospheric pressure to desorb the water and ethanol on the dessicant from a previous dehydration cycle, and reversing the flow through the two beds after the temperature of the first bed increases no more than about 14° C. (25° F.).

5 Claims, 1 Drawing Figure

U.S. Patent    Oct. 4, 1983    4,407,662
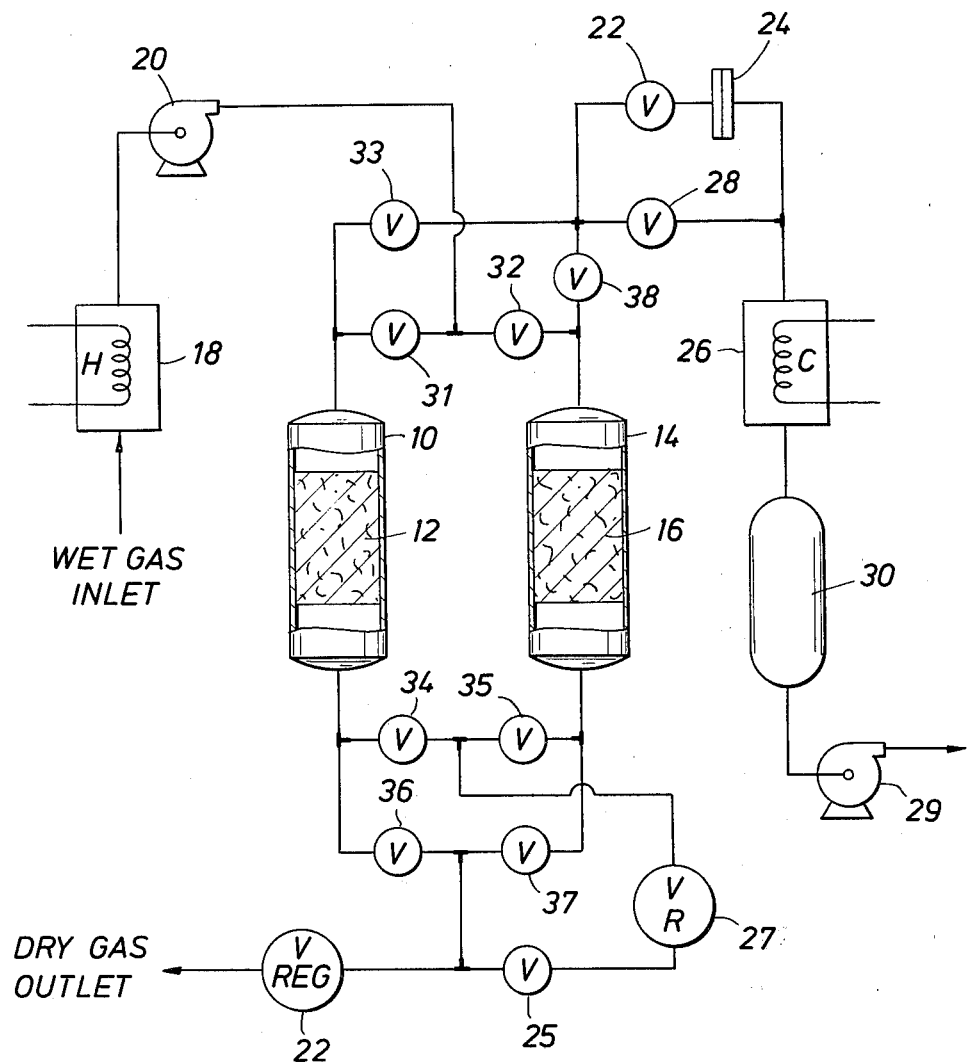

METHOD OF REMOVING WATER FROM ETHANOL

This is a continuation of application Ser. No. 198,370 filed Oct. 20, 1980, and entitled "A Method of Removing Water from Ethanol, now abandoned."

This invention relates to processes for dehydrating ethanol generated by ethanol distillation columns to obtain an ethanol that can be used as a motor fuel or mixed with gasoline to produce a motor fuel, such as gasohol.

Ethanol can be readily produced by fermentation processes which yield a dilute aqueous solution of ethanol, normally 8% to 10% by weight. Further concentration of the ethanol by traditional distillation processes usually is used to produce an azeotrope containing about 5% water by weight. For some motor fuel uses, such as when mixed with gasoline to produce gasohol, the ethanol must be substantially anhydrous, and therefore further azeotropic distillation is required. The energy requirement for the azeotropic distillation is very high and various means for the production of essentially anhydrous alcohol by more energy efficient means have been reported.

See Hartline, "Lowering the Cost of Alcohol," *Science*, (Vol. 206, 41-96 1979).

See also D. E. Eakin, J. M. Denovan, G. R. Cysenski, S. E. Petty, and J. V. Maxham's Report prepared for the U.S. Department of Energy under Contract DE-AC06-76RLO 1830 by Pacific Northwest Laboratory, operated by Batelle Memorial Institute.

Both of these articles report the use of dehydration agents to selectively adsorb water from solutions of alcohol. Eakin, et al., report the use of CaO as the dehydrating agent. All of the reported dehydration processes are based on using liquid distillate normally containing 80% to 95% by weight of alcohol (160-190 proof). In U.S. Pat. No. 2,137,605, Derr reports the use of alumina as the dehydrating agent in a vapor phase drying operation. All of the reported processes using various dehydrating agents have the shortcoming of either co-adsorbing substantial quantities of alcohol during the adsorption of water or they require considerable quantities of energy for the regeneration of the adsorbent.

It is known that modified zeolites, which are sold commercially as molecular sieves by the Linde Division of Union Carbide and by Davison Chemical, a Division of W. R. Grace & Co., are capable of removing water from both liquid and gaseous mixtures containing water. It is further known that by the utilization of molecular seives with the proper pore size, it is possible to adsorb water preferentially from both liquids and gases, if the water molecules are the smallest molecules present in the system. Prior to the present invention, the use of molecular sieves has not been suggested for producing essentially anhydrous ethanol from gaseous ethanol vapors containing water vapor using a pressure swing system with relatively short cycle times, and it is an object of this invention to provide such a method.

It is a further object to provide a method of producing anhydrous ethanol (199 proof) that reduces substantially the BTU's per gallon required.

SUMMARY OF INVENTION

The present invention provides a practical and efficient low energy process for concentrating ethanol from aqueous vapors thereof. The water is removed by adsorption on the molecular sieves. Although it was known that water can be adsorbed preferentially on molecular sieves, as far as is known, molecular sieves have not been used as a basis of a process for producing essentially anhydrous ethanol from aqueous vapors thereof. When water is being adsorbed on the metal alumina silicates, known generally as molecular sieves, the pores of the molecular sieve accept the water molecules, but essentially none of the ethanol vapor. Care must be taken to stop the flow of aqueous alcohol vapors through the column before breakthrough takes place.

During the experimental work leading to the present invention, it was discovered that the adsorbed water can be efficiently removed from the molecular sieve by passing a stream of essentially anhydrous alcohol vapor through the column. In a preferred embodiment, the water is removed under reduced pressure, and the alcohol-water vapor mixture is condensed.

DETAILED DESCRIPTION

The adsorbant to be used in practicing the present invention is crystalline metal aluminosilicate known as molecular sieve. More specifically, the molecular sieve is known generally as 3A molecular sieve with openings of about 3Å. Such an adsorbant is available commercially from the Linde Division of Union Carbide Corporation, Tarrytown, N.Y. or Davison Chemical, a Division of W. R. Grace and Company, Baltimore, Md.

It should be understood that this invention is not directed to a specific adsorbant, although 3A molecular sieve is preferred for the commercial practice of this invention.

In general, the process of the invention can be applied to any alcohol vapor from which it is desired to remove essentially all water. Usually the ethanol vapors to be dehydrated will be at least 80% ethanol by weight. Alcohol vapors of this concentration can be readily produced by standard distillation processes, however, in some embodiments, if desired, aqueous alcohol of at least 80% by weight ethanol may be vaporized directly at the location of the unit described in this invention. In general, therefore, the process of the present invention is applicable to the treatment of ethanol vapors containing as little as 80% ethanol by weight.

The drawing shows the best mode of the invention.

In carrying out the process, a granular bed of molecular sieves are contained within a column arranged for the passage of vapors therethrough. The feed stock being processed is passed through the bed until the molecular sieve becomes loaded with water to a preselected depth below its upper level as determined by monitoring the concentration of ethanol vapors passing out of the bed or by observing the temperature changes within the bed. Preferably, the temperature of the bed should increase between 11°-14° C. (20°-25° F.). The adsorption temperature has to be controlled to maintain the temperature above the boiling point of the ethanol vapors being employed. To this end, a heater has been installed at the inlet of the unit to pre-heat the alcohol vapors to at least 75° C. but generally the vapors are preheated to 90° C. (194° F.) to 120° C. (248° F.). As stated above as the water vapor is being adsorbed by the adsorption agent, the temperature of the adsorption agent rises. Usually, the maximum allowed temperature in the adsorption column is held to about 125° C. (257° F.). This keeps the vapor in a superheated state well above the boiling point of the water and alcohol mixture, since 190 proof alcohol boils at 78° C. In the accompanying drawing a diagrammatic flow sheet for carrying out the method of the invention is shown.

Two separate beds of desiccant are used in the process of this invention. This allows a continuous operation with one bed drying ethanol while the other bed is being purged of water vapor that it has adsorbed previously while it was drying ethanol. Thus, vessel 10 contains first bed 12 of a desiccant selected to adsorb water, but not ethanol. One such desiccant known to accomplish this is a type 3Å molecular sieve. Second vessel 14 is also provided with bed 16 of such a desiccant. The wet ethanol gas, either directly from a distillation column or from a storage tank, is passed first into blower 20, which makes sure that a positive pressure is maintained on the ethanol entering the upper end of vessel 10. This pressure should be maintained at between 2–10 psig. It then flows through heat exchanger 18, where it is heated to a temperature of between 82.2°–121° C. (180°–250° F.). When the gas comes directly from a distillation tower, this heating step may not be required. The wet ethanol then passes downwardly through vessel 10 and desiccant bed 12 where the water vapor is removed and the dry gas flows to the outlet through back pressure regulating valve 22, which holds a constant minimum pressure in the vessel.

All of the dried gas does not flow out of the outlet. Some of it is used to regenerate bed 16, which has previously been drying ethanol. Depending upon the circumstances some ten to thirty percent of the dried ethanol leaving vessel 10 will be diverted into the lower end of vessel 14 for this purpose. Prior to the introduction of the dried ethanol into the bottom of vessel 10, the vessel is depressurized. This is accomplished by opening valve 22 to let the pressurized gas in the vessel flow upwardly out of the vessel. The gas flows through valve 22 and orifice 24 into condenser 26. Orifice 24 is used to insure that the pressurized gas in the vessel does not flow too rapidly out of the vessel and create undesirable turbulence in the desiccant.

After the vessel has been depressurized, valve 25 in opened and regulating or throttling valve 27 allows the ten to thirty percent of the dried ethanol leaving vessel 10 to flow upwardly through desiccant bed 16 to regenerate it. At this time, valve 28 is opened to bypass orifice 24 so that the flow of the ethanol upwardly through the bed will not be unduly impeded. As the gaseous mixture of ethanol and water vapor reach condenser 26, it is cooled sufficiently to condense both the ethanol and water, which reduces the pressure in vessel 14 below atmospheric, preferably below 5 psia. A vacuum pump can also be used to help lower the pressure to the desired amount. The condensed ethanol and water flow from the condenser into sump tank 30 from where it can be recycled to the distillation tower by pump 29.

During operation; the adsorbent at the end of the bed that is first contacted by the ethanol-water vapor mixture will be virtually saturated with water while the adsorbent at the other end of the bed will be virtually dry. In between, the amount of water collected by the adsorbent will vary along a substantially straight line between the two extremes. When dehydrating the line will shift toward a higher percentage of water on the adsorbent and it will shift toward a lower percentage as the bed is regenerated. It will not, however, become completely saturated or completely regenerated.

As explained above, during dehyration the bed temperature will rise. Conversely, during degeneration the bed temperature will tend to drop. The total swing should be kept below 22° C. (40° F.).

While bed 12 is drying and bed 16 is being regenerated, valves 32,33, 34, and 37 are closed and valves 31, 34, and 36 are open. After bed 16 has been regenerated, the process is reversed.

Valves 31, 35, and 36 are closed and valves 32, 33, 34, and 37 are open. Now the wet ethanol vapor is pumped into the upper end of vessel 14 to be dried as it moves downwardly through bed 16. At the same time the purging operation of bed 12 begins in the same manner as described above.

The cycle time, the time that one bed will be drying while the other one is being purged, will vary from between 2 to 30 minutes depending upon the amount of water vapor in the ethanol being dried, the volume of ethanol being dehydrated, and the size of the bed.

From the foregoing, it will be seen that this invention is one well adapted to attain all of the ends and objects hereinabove set forth, together with other advantages that are obvious and that are inherent to the method.

I claim:

1. A method of removing sufficient water from $H_2O$ ethanol at least 160 proof to produce ethanol having a proof of 195 or more comprising the steps of heating the ethanol water mixture until it is a vapor with sufficient superheat to maintain the vapor phase and prevent substantial capillary adsorption as the mixture passes through a dessicant bed of molecular sieves, passing the superheated ethanol water mixture through the bed to remove sufficient water to increase the proof of the ethanol to at least 195, passing a portion of the dehydrated ethanol through a second dessicant bed of molecular sieves at less than atmospheric pressure to desorb the water and ethanol on the dessicant from a previous dehydration cycle, and reversing the flow through the two beds after the temperature of the bed increases no more than about 14° C. (25° F.).

2. The method of claim 1 in which the incoming ethanol is heated to 90°–120° C. (194°–248° F.).

3. The method of claim 1 in which the pressure of the ethanol vapor is 2–10 PSIG.

4. The method of claim 1 in which the ethanol is heated to a temperature of 99°–110° C. (210°–230° F.) at 2–10 PSIG.

5. A method of dehydrating ethanol to 195 proof or higher comprising the steps of heating the ethanol to 99°–110° C. (210°–230° F.) at a pressure of 2–10 PSIG, passing the gaseous ethanol through a first dessicant bed of 3Å molecular sieves with sufficient superheat to prevent substantial capillary adsorption as the mixture passes through said bed, for 2–10 minutes where a portion of the water and the ethanol is adsorbed by the dessicant bed, passing a portion of the dehydrated gaseous ethanol through a second dessicant bed of 3Å molecular sieves at 5–10 PSIA to desorb the water and ethanol adsorbed by the bed previously when gaseous ethanol was passed through the bed at 99°–110° C. (210°–230° F.) and 2–10 PSIG pressure, diverting the flow of the gaseous ethanol to the second bed and the flow of the desorbing ethanol to the first bed at the end of the 2–10 minute cycle, and repeating the diverting step at the end of each 2–10 minute cycle such that the temperature of the first bed increases no more than about 14° C. (25° F.).

* * * * *